(12) United States Patent
Burton et al.

(10) Patent No.: US 9,242,076 B2
(45) Date of Patent: Jan. 26, 2016

(54) ULTRASONICALLY VISIBLE SCORING BALLOON

(75) Inventors: David G. Burton, Bloomington, IN (US); Per Elgaard, Haslev (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 361 days.

(21) Appl. No.: 13/599,435

(22) Filed: Aug. 30, 2012

(65) Prior Publication Data

US 2013/0060127 A1 Mar. 7, 2013

(30) Foreign Application Priority Data

Sep. 2, 2011 (GB) .................................. 1115204.8

(51) Int. Cl.
- *A61B 5/05* (2006.01)
- *A61M 25/10* (2013.01)
- *A61B 17/3207* (2006.01)
- *A61B 19/00* (2006.01)
- *A61B 17/22* (2006.01)

(52) U.S. Cl.
CPC ........ *A61M 25/10* (2013.01); *A61B 17/320725* (2013.01); *A61B 19/54* (2013.01); *A61B 2017/22061* (2013.01); *A61B 2019/5425* (2013.01); *A61B 2019/5454* (2013.01); *A61M 2025/1079* (2013.01); *A61M 2025/1086* (2013.01)

(58) Field of Classification Search
USPC ............................ 600/424, 564, 570; 606/159
See application file for complete search history.

(56) References Cited

U.S. PATENT DOCUMENTS

| 5,336,178 A | 8/1994 | Kaplan et al. |
| 5,383,460 A | 1/1995 | Jang et al. |
| 5,429,136 A | 7/1995 | Milo et al. |
| 5,507,292 A | 4/1996 | Jang et al. |
| 5,571,086 A | 11/1996 | Kaplan et al. |
| 5,704,913 A * | 1/1998 | Abele et al. ............... 604/101.02 |
| 6,306,151 B1 * | 10/2001 | Lary ............................. 606/159 |
| 7,008,438 B2 * | 3/2006 | O'Brien ....................... 606/159 |
| 2002/0010489 A1 | 1/2002 | Grayzel et al. |

(Continued)

FOREIGN PATENT DOCUMENTS

| WO | WO 93/19800 | 10/1993 |
| WO | WO 93/19800 A1 | 10/1993 |

(Continued)

OTHER PUBLICATIONS

Electronic Filing Receipt for UK Patent application No. GB 1115204.8 mailed Sep. 2, 2011.
Combined Search and Examination Report for GB Application No. 1115204.8 mailed Dec. 6, 2011.

(Continued)

*Primary Examiner* — Long V Le
*Assistant Examiner* — Ellsworth Weatherby
(74) *Attorney, Agent, or Firm* — Brinks Gilson & Lione

(57) ABSTRACT

An angioplasty balloon (40) is provided with a plurality of scoring elements (44) extending along the balloon (40). Within the scoring element (44) there are provided channels or lumens (36) extending therethrough. The channels or lumens (36) provide for Rayleigh scattering of ultrasonic waves directed to the balloon (40), thereby being visible by imaging devices. The channels or lumens (36) provide visibility of the balloon (40) during medical procedures, both when the balloon (40) is in a deflated, wrapped, condition and also when the balloon (40) is inflated. It is not necessary to use contrast media to fill the balloon (40).

9 Claims, 2 Drawing Sheets

(56) References Cited

U.S. PATENT DOCUMENTS

| | | |
|---|---|---|
| 2003/0144683 A1* | 7/2003 | Sirhan et al. ............... 606/194 |
| 2005/0070888 A1 | 3/2005 | Dimatteo et al. |
| 2005/0222596 A1 | 10/2005 | Maschke |
| 2008/0300610 A1* | 12/2008 | Chambers ................ 606/159 |
| 2010/0069837 A1 | 3/2010 | Rassat et al. |

FOREIGN PATENT DOCUMENTS

| | | |
|---|---|---|
| WO | WO 96/30064 A1 | 10/1996 |
| WO | WO 98/10824 | 3/1998 |
| WO | WO 98/10824 A1 | 3/1998 |
| WO | WO 03/049603 A2 | 6/2003 |
| WO | WO 03/072178 A1 | 9/2003 |
| WO | WO 2005/115522 A2 | 12/2005 |
| WO | WO 2007/102909 A2 | 9/2007 |
| WO | WO 2011/096983 A1 | 8/2011 |

OTHER PUBLICATIONS

Response to Combined Search and Examination Report under Sections 17 and 18(3) for UK Patent application No. GB1115204.8 mailed Jun. 7, 2012.

Examination Report under Section 18(3) mailed Jul. 6, 2012, for UK Patent application No. GB1115204.8.

Response to Examination Report under Section 18(3) mailed Aug. 14, 2012, for GB Patent Application No. 115204.8.

Examination Report for GB Patent Application Serial No. 1115204.8 dated Aug. 31, 2012, 1 page.

Extended Search Report for European Application Serial No. 12 27 5128 dated Dec. 3, 2012, 6 pages.

Examination Report for GB Patent Application Serial No. 1115204.8 dated Jun. 20, 2013, 2 pages.

Examination Report for GB Patent Application Serial No. 1115204.8 dated Aug. 23, 2013, 2 pages.

Examination Report for GB Patent Application Serial No. 1115204.8 dated Oct. 23, 2013, 2 pages.

* cited by examiner

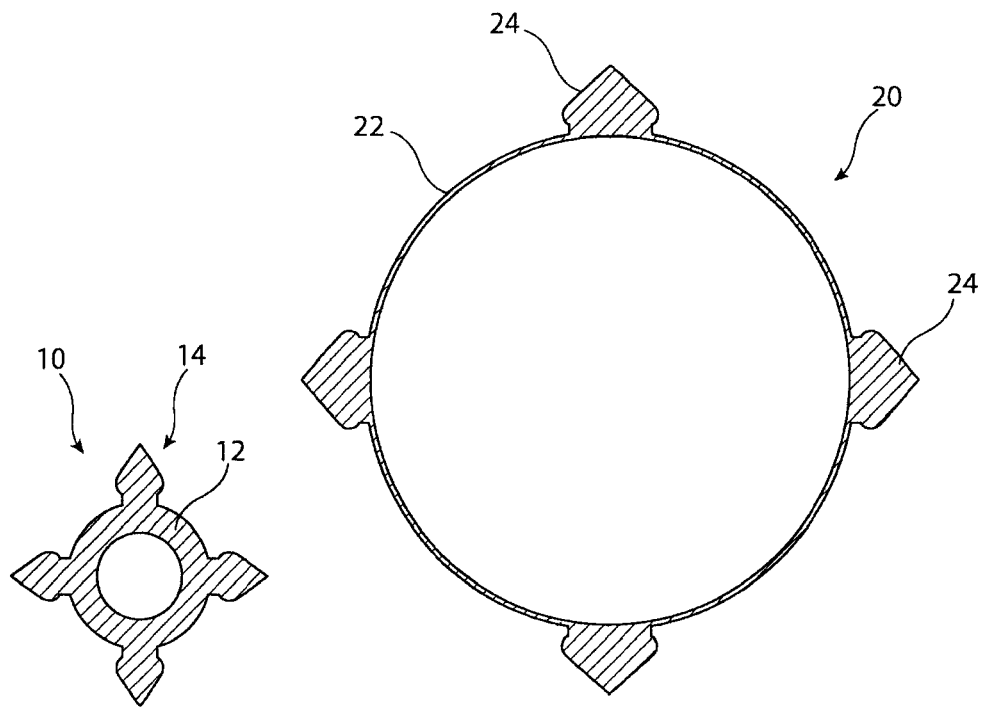
Figure 1a
Figure 1b
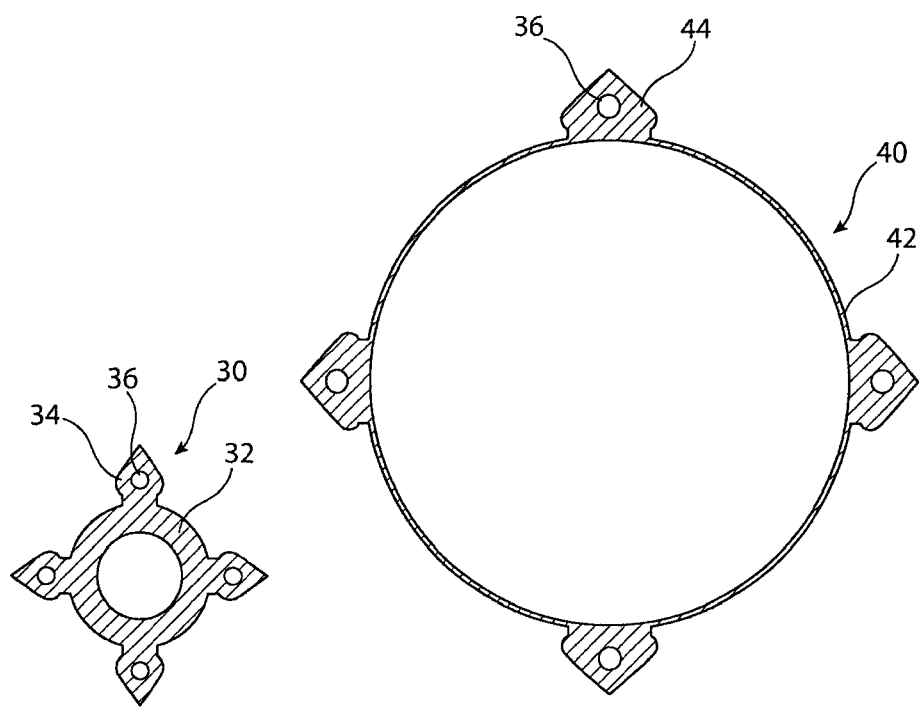
Figure 2a
Figure 2b

ULTRASONICALLY VISIBLE SCORING BALLOON

CROSS-REFERENCE TO RELATED APPLICATIONS

This application claims priority to GB application No. 1115204.8, filed Sep. 2, 2011, titled "Ultrasonically Visible Scoring Balloon", the contents of which are incorporated herein by reference.

TECHNICAL FIELD

The present invention relates to medical balloons and preferably to scoring or cutting balloons for use, for example, in angioplasty procedures.

BACKGROUND ART

The use of cutting or scoring balloons for angioplasty and other procedures is well documented. Typically, such balloons are made of a thin but strong material, Pebax being one example, which is able to be wrapped into a very small diameter and yet which is strong when inflated. Cutting or scoring balloons typically have one or more cutting or scoring elements provided on or in the balloon wall which extend beyond the perimeter of the balloon wall in a radially outward direction. These cutting or scoring elements may be formed of a stiff material, even of metal, which is attached to the balloon, for instance by bonding or adhesion. In other embodiments, the cutting or scoring elements may be formed integrally with the balloon wall, and they may be made of different material from that of the remainder of the balloon.

As a result of the structure and materials used for such scoring balloons, they are not particularly suited for traditional angiographic imaging techniques, particularly ultrasonic imaging, thereby having to rely upon less advantageous CRT and MRI imaging. Specifically, such balloons tend to be very difficult to see and in some instances can be virtually invisible. In order to mitigate these disadvantages, such balloons can be inflated with a contrast media which is opaque under ultrasonic imaging. However, suitable contrast media does not resolve the imaging difficulties when the balloon is in its deflated condition. Moreover, contrast media tends to be relatively more viscous than other fluids which can be used to inflate such balloons, with the result that the time required for inflation and deflation of a balloon with contrast media is increased. The increased viscosity also limits the minimum diameter of the inflation and deflation lumen and therefore the minimum achievable diameter of the balloon catheter.

Balloon catheters suitable for imaging are disclosed, for example, in US-2005/0222596, U.S. Pat. No. 5,507,292, U.S. Pat. No. 5,429,136 and U.S. Pat. No. 5,383,460.

DISCLOSURE OF THE INVENTION

The present invention seeks to provide an improved medical balloon and in particular one which is more readily visible by imaging, in particular ultrasonic or magnetic imaging.

According to an aspect of the present invention, there is provided a medical angioplasty balloon for endoluminal location within a patient, the balloon including a balloon wall extending in the direction of a longitudinal axis of the balloon and provided with one or more scoring or cutting elements, there being embedded within the one or more scoring or cutting elements an elongate channel or lumen providing a material discontinuity therewithin.

The at least one lumen or channel provides a radiopaque or echogenic element in the balloon useful in giving the balloon visibility under imaging. More specifically, the material discontinuity of the channels affects the passage of ultrasonic or magnetic waves directed to the balloon.

A discontinuity of such a nature in the balloon wall provides within the structure of the balloon an inherent property which is visible when ultrasonic or magnetic waves are directed to the balloon. It is therefore not necessary to rely upon contrast media for inflating the balloon in order to make the balloon visible under imaging.

In the preferred embodiment, the discontinuity is shaped so as to generate Rayleigh scattering of ultrasonic or magnetic waves.

Advantageously, the one channel or lumen is at least partially rounded. Most preferably, the at least one channel or lumen is substantially round in axial cross section and is hollow or filled. In an embodiment, the or each channel or lumen is filled with air or a gas, in other embodiments it may be filled with a gel or rod of polymeric material, metal or metal alloy.

The at least one channel advantageously provides a feature in the balloon wall which has a material of density different from the density of the material forming the balloon wall, that is of a lower or higher density than that of the material forming the balloon.

The at least one channel or lumen may extend in the longitudinal direction of the balloon or may extend at an angle thereto. For instance, in some embodiments, the at least one channel is substantially straight while in other embodiments it or they may expend helically along the length of the balloon.

It is preferred that the at least one such scoring element extends in a longitudinal direction of the balloon.

It has been found that a channel or lumen with a diameter of less than about 100 micrometers does not adversely affect the strength or performance of the balloon and yet provides good imaging characteristics. Most preferably, each channel or lumen has an inner diameter of substantially 50 micrometers.

According to another aspect of the present invention, there is provided a method of monitoring a medical angioplasty balloon within a patient, which balloon is provided with a balloon wall extending in the direction of a longitudinal axis of the balloon and provided with one or more scoring or cutting elements, there being embedded within the one or more scoring or cutting elements an elongate channel or lumen providing a material discontinuity therewithin; the method including the steps of inserting the balloon into the body of a patient, directing ultrasonic or magnetic wave energy to the patient; detecting the ultrasonic or magnetic wave energy reflected or scattered from said patient by the at least one channel or lumen and determining from the detected wave energy the location and/or condition of scoring or cutting elements of the balloon.

Advantageously, the determination step monitors for the relative position of a plurality of said channels, in order to determine a shape of the balloon and/or a state of inflation of the balloon.

BRIEF DESCRIPTION OF THE DRAWINGS

Embodiments of the present invention are described below, by way of example only, with reference to the accompanying drawings, in which:

FIGS. 1A and 1B are, respectively, transverse cross-sectional views of a balloon raw material tube and an inflated balloon provided with no ultrasonically visible elements embedded therein;

FIGS. 2A and 2B are, respectively, transverse cross-sectional views of an embodiment of balloon raw tubing and inflated balloon.

DESCRIPTION OF THE PREFERRED EMBODIMENTS

Figure 3:
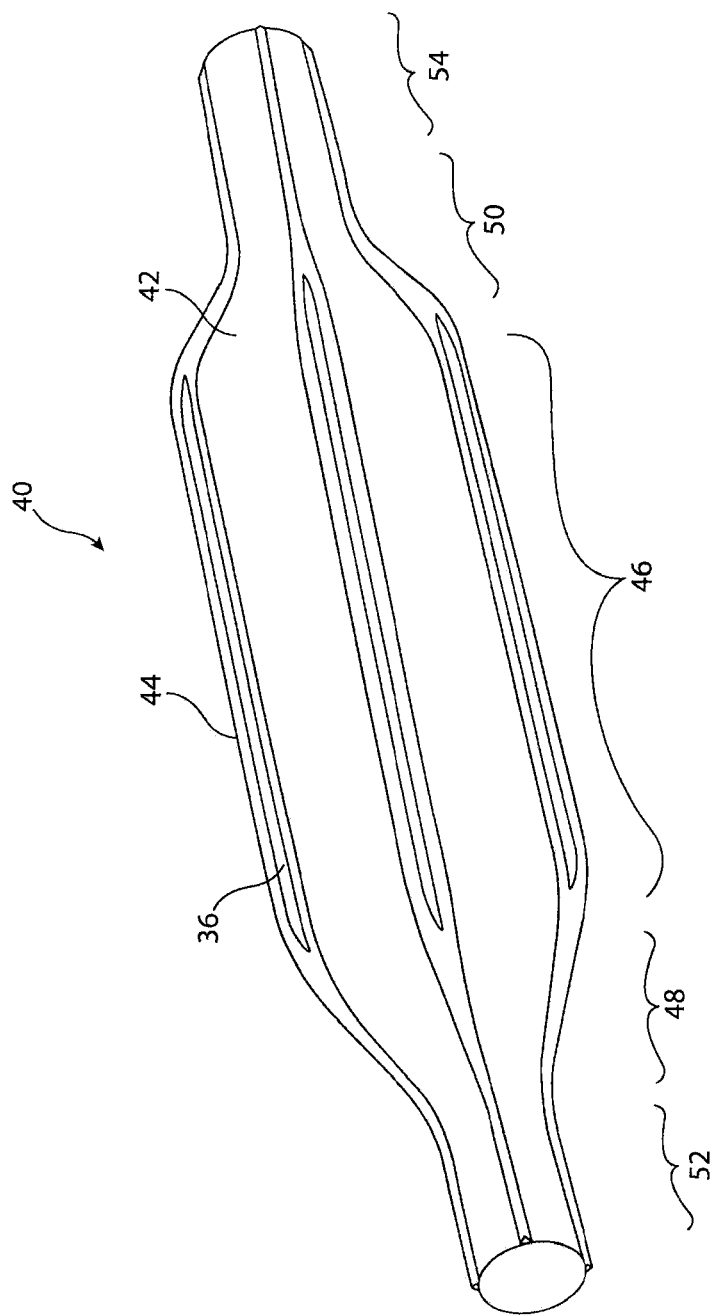
FIG. 3 is a perspective view of an embodiment of scoring balloon according to FIGS. 2A and 2B.

Described below are various embodiments of a scoring balloon provided with one or more echogenic elements. By echogenic it is meant elements which are visible to imaging, in the preferred embodiment to ultrasound imaging. As will be apparent from the teachings herein, the preferred embodiments provide elements which contribute or cause Rayleigh scattering of ultrasonic wave energy, although the elements could otherwise be absorbent (radiopaque) or reflective of ultrasonic waves.

Although the preferred embodiments relate to scoring or cutting balloons, as indicated below the teachings herein are applicable also to other types of balloon which do not necessarily perform a scoring or cutting function.

Referring to FIGS. 1A and 1B there is shown in schematic form transverse cross-sectional views of, respectively, a balloon raw tubing and of an inflated balloon. The balloon shown in FIGS. 1A and 1B is a scoring balloon.

Referring to FIG. 1A, the raw tubing 10 has a first element 12 which is of tubular form. Integral and extending regularly therefrom are, in this example, four ribs 14 which extend along the length of the tubing.

Raw tubing 10 is made of a material such as nylon, Pebax (polyether block amide), PET, polyethylene, polyurethane and the like. It can be made of any material which is able to be inflated and drawn to the balloon shape shown in FIG. 1B. The material may be such as to cause the balloon to be non-compliant or compliant.

With reference to FIG. 1B, the final inflated balloon 20 has a balloon wall 22 which is considerably thinner than that of the raw tubing 10, caused principally by stretching the body element 12 of the tubing 10 during the balloon formation process. Extending from the balloon 22 are four scoring elements 24 which run along the length of the balloon 22. These scoring elements 24 are formed from the ribs 14 of the raw tubing 10. In a typical procedure, the raw tubing 10 is inflated within a mould which has a plurality of channels or recesses within the mold chamber of a shape, size and position to accommodate the ribs 14 and thereby for use in ensuring that the ribs do not flatten on inflating of the tube 12.

The scoring elements 24 may extend in a longitudinal direction of the balloon 22 but in other embodiments may extend at an angle to this, for example helically.

It is preferred, as with the embodiments described with reference to FIGS. 2 and 3 below, that the ribs 14 and balloon tubing 12 are formed of the same material as one another, and typically by co-extrusion through a suitable die. It is not excluded, however, that the ribs 14 and tubing 12 can be formed of different materials, in dependence upon, primarily, the characteristics of stiffness and strength desired for the scoring elements 24 formed from the ribs 12.

The scoring balloon shown in FIG. 1B is typically of low echogenicity and radiopacity. In other words, it is not readily visible by ultrasonic or magnetic imaging techniques. In order to make the balloon 20 visible, this can be inflated with a contrast media which is opaque during imaging. Although the use of contrast media does improve the echogenicity of such balloons, there is the risk of leakage of contrast media into the patient should the balloon tear. Furthermore, as contrast media is relatively viscous compared to, for example, water or saline solution, the use of contrast media results in longer inflation and deflation times for the balloon 20. This viscosity of the contrast media also limits the minimum size of the inflation/deflation lumen and therefore of the diameter of the introducer assembly.

Furthermore, with contrast media the balloon remains substantially invisible when in the patient until contrast media is injected therein. As a result, it is difficult to determine the position and shape of the balloon when it is in a deflated state.

Referring now to FIGS. 2A and 2B, there is shown a preferred embodiment of scoring balloon provided with echogenic elements therein.

More specifically, the balloon raw tubing 30, shown in FIG. 2A has a tube portion 32 equivalent to a tube portion 12 of the raw tubing 10 in FIG. 1A and a plurality of longitudinally extending ribs 34. The ribs 34 have extending therethrough a lumen or channel 36 (hereinafter referred to as a channel). The ribs 34 and channels 36 extend, in this embodiment, for the whole length of the tube portion 32.

The channels 36 are formed in the raw tubing by means of a suitable die. In this regard, current extrusion technology can extrude channels or lumens of diameters of the order of tens of micrometers. The channels 36 can be made by any of the known technologies and in one embodiment extend for the whole length of the raw tubing. The channels 36 may be fattened at the ends of the balloon when this is formed from the raw tubing. The channels 36 can have a diameter of the order of tens of micrometers, one example being in the region of 50 micrometers.

As in the examples of FIGS. 1A and 1B, the raw tubing of FIG. 2A is inflated within a suitable heated mold so as to expand the tubing into the final balloon shape shown in FIG. 2B. In particular, in the preferred embodiment, the mold is provided with internal grooves in its inner wall of a position, size and shape able to accommodate the form of the ribs 34 and to prevent these from being stretched during the stretching of the tubing 12 to form the balloon wall. Preservation of the form of the ribs 34, to form the scoring elements of the balloon, will also preserve the form and structure of the channels 36.

As a result, as can be seen in FIG. 2B, the channels 36 also exist in the scoring elements 44 of the final balloon form. The balloon wall 42 can be of conventional thickness and therefore can exhibit the same characteristics as known medical balloons.

The balloon of FIG. 2B can be seen in its complete form in FIG. 3. As is conventional with such medical balloons, the balloon 40 includes a central or body portion 46 which is substantially cylindrical, although could be molded into a different shape if desired. First and second cone portions 48, 50 are located, respectively, at either end of the body portion 46. First and second neck portions 52, 54 bound, respectively, the first and second cone portions 48, 50. The neck portions 52, 54 are typically bonded, secured by other means or otherwise integral with a balloon catheter (not shown in FIG. 3).

The scoring elements 44 extend, in this embodiment, along the entire length of the balloon 40, including over the conical portions 48, 50 and the neck portions 52, 54. The channels 36, in this embodiment, extend along the entire length of the scoring elements 44 and thus along the entire length of the balloon 40 and in particular across the body portion 46.

The balloon 40 could be made of conventional compliant or non-compliant materials including, for example, polyurethane, Pebax (polyether block amide), nylon, polyethylene, PET and the like, as with the example of FIGS. 1a and 1b.

The channels 36 are preferably cylindrical and are substantially circular in transverse cross-section. In the preferred embodiment they are filled with air or other gas. They advantageously have a relatively small diameter, typically of no more than around 100 micrometers, in the preferred embodiment of around 50 micrometers. It is preferred these channels have a diameter which is smaller than the wavelength of ultrasound used in medical imaging.

The channels 36 provide a material discontinuity within the structure of the balloon 40 which affects the passage of imagining wave energy directed to the balloon. The substantially circular cross-sectional shape of the preferred embodiment of channels 36 provides a circular or rounded material discontinuity which promotes Rayleigh scattering of ultrasonic waves directed through the balloon. This scattering causes the channels to look opaque or darkened in the image and thus to be visible. They could therefore be described as echogenic elements.

As will be apparent from the view of FIG. 3, a balloon provided with a plurality of such channels 36 extending along the scoring elements 44 in the manner shown will generate a plurality of visible lines during imaging, which lines are indicative of the position of the balloon 40, the state of inflation of the balloon, the shape of the balloon and the location and shape of the scoring elements 44. The channels 36 and thus these characteristics of the balloon are visible irrespective of the state of inflation of the balloon. Specifically, the balloon 40 will be visible when it is deflated and also when it is deployed.

As a result, the location of the balloon can be readily seen within a body vessel when still in a wrapped configuration, thereby enabling the clinician to position the balloon 40 accurately at the desired site within the patient.

Furthermore, the channels 36 and thus profile of the balloon 40, are visible by imaging in the course of inflation of the balloon towards its fully deployed configuration, enabling the clinician to determine how the balloon is inflating and also the shape and characteristics of the body vessel within which the balloon is being deployed. Any obstructions, constrictions or non-cylindrical profiles of the vessel will be apparent by the imaged shape of the channels 36. Specifically, any such vessel features are likely to constrict the inflation of the balloon 40, preventing it from reaching its fully inflated cylindrical shape. As a result, one or more of the scoring elements 44, and thereby channels 36, are likely not to be straight but will be curved or bent around the constriction or obstruction of the vessel wall. This shape of the channel or channels 36 will thus provide in the obtained image an indication of the internal shape of the vessel wall at that location.

Moreover, the channels 36, when located in the scoring elements 44, assist the clinician in viewing the progress of an angioplasty treatment. In the latter case, the clinician can see the effectiveness of the scoring or cutting action in removing stenotic material.

The visibility of the balloon is not dependant upon the use of contrast media for inflation, although it is not excluded that contrast media could be used. The balloon could be inflated using other fluids, such as saline solution, which are less viscous and which can thus assist in faster inflation and deflation of the balloon 40, as well as requiring a smaller inflation and deflation lumen and thus allowing a smaller diameter introducer assembly.

The resultant balloon 40 can be used also in the treatment of vessels in the extremities, such as the venous fistula and similar patient locations.

The embodiment described above has channels 36 which are empty, that is, filled with air or other gas. It is also envisaged that the channels 36 could be filled with other materials, for instance radiopaque or wave scattering materials in the form of a fluid, powder or solid element such as a rod. Any element or material which provides for Rayleigh scattering of ultrasonic waves or which otherwise is radiopaque could be suitable. It is preferred that It is not essential that every scoring element be provided with a channel and it is envisaged in some embodiments that only one or more scoring element could be provided with such a channel 36. Similarly, even though the embodiment described above has the scoring elements 44 and channels 36 extend over the whole of the length of the balloon 40, other embodiments may have these extend over only a part of the balloon. For instance, the channels 36 could extend over only the body portion of the balloon 40. The latter could be achieved by having the scoring elements extend also by this more limited extent or by removing the channels and/or scoring elements at the location of the conical and neck portions of the balloon, for instance by cutting or heat pressing the scoring elements during or after formation of the balloon 40 from the raw tubing.

Moreover, in some structures of balloon, there may also be provided more than one channel 36 within each scoring element 44.

It is also envisaged that the channels 36 need not be continuous for the whole length of the balloon 40 or even of the scoring elements 44. They could, for example, be in the form of a series of separate, serially aligned channels 36 within the scoring elements 44.

The scoring elements 44 need not extend longitudinally along the length of the balloon 40 but could in other embodiments extend in other directions, for example helically.

It is envisaged in other embodiments that channels 36 could be provided within the balloon wall 40 rather than being radially spaced therefrom within the scoring elements 44. In such an alternative, the balloon need not necessarily be provided with scoring elements. The channels 36 could be located in a part of the balloon wall which is thicker than other parts of the balloon wall which do not have channels therein or could simply be provided within a balloon wall of even thickness throughout the circumferential extent of the balloon.

Thus, it will be appreciated that the provision of echogenic elements, that is channels or lumens, within a balloon, is not necessarily restricted to a balloon used for angioplasty procedures only. It could be provided with a balloon used for other medical purposes, for instance for lumen occlusion as well as for balloons used for expanding stents or other medical devices within the lumen of a patient.

The scoring elements 44, or otherwise parts of the balloon within which the channels 36 are located, could be the same material as the balloon wall or the remainder of the balloon wall, or could otherwise be formed within scoring elements of the portion of the balloon which is of a different material.

Similarly, the channels 36 could be provided within a base element to which a separate cutting or scoring element is attached, such as a cutting blade.

The above described embodiments have four scoring elements and four channels. This is the preferred number, although in other embodiments there may be fewer channels and in other more, for instance, two, three, five or six.

It is to be understood that only some embodiments are described above which would be apparent to the skilled person having regard to the teachings herein and that the described embodiments are not intended to be limiting of these teachings.

Although the claims are set out in single claim dependent form, it is to be understood that the claimed and disclosed features herein can be combined with one another and that the claims are intended to be interpreted as covering these combinations as if they were in multiple dependent form.

The invention claimed is:

1. A medical angioplasty balloon for location within a lumen of a patient, the balloon including a balloon wall extending in the direction of a longitudinal axis of the balloon and provided with one or more scoring or cutting elements, there being embedded within the one or more scoring or cutting elements an elongate channel or lumen having proximal and distal ends, completely circumscribed and enclosed by the balloon wall, sealed at its proximal and distal ends, and filled with a gas, the channel or lumen thereby providing a material discontinuity therewithin to increase ultrasonic visibility.

2. A medical balloon according to claim 1, wherein the at least one channel or lumen is substantially round in axial cross-section.

3. A medical balloon according to claim 1, wherein the at least one such scoring element extends in a longitudinal direction of the balloon.

4. A medical balloon according to claim 1, wherein the scoring element is integral with the balloon.

5. A medical balloon according to claim 1, wherein the at least one scoring element is formed of the same material as the balloon.

6. A medical balloon according to claim 4, where in the at least one channel or lumen has a diameter of less than 100 micrometers.

7. A method of monitoring a medical angioplasty balloon within a patient, which balloon is provided with a balloon wall extending in the direction of a longitudinal axis of the balloon and provided with one or more scoring or cutting elements, there being embedded within the one or more scoring or cutting elements an elongate channel or lumen having proximal and distal ends, completely circumscribed and enclosed by the balloon wall, sealed at its proximal and distal ends, and filled with a gas, the channel or lumen thereby providing a material discontinuity therewithin to increase ultrasonic visibility; the method including the steps of inserting the balloon into the body of a patient, directing ultrasonic or magnetic wave energy to the patient; detecting the ultrasonic or magnetic wave energy reflected or scattered from said patient by the at least one channel and determining from the detected wave energy the location and/or condition of scoring or cutting elements of the balloon.

8. A method according to claim 7, wherein the determination step monitors for the shape of said channels in order to determine a shape of the balloon and/or a state of inflation of the balloon.

9. A method according to claim 7, wherein the determination step monitors for the relative position of a plurality of said channels, in order to determine a shape of the balloon and/or a state of inflation of the balloon.

* * * * *